US008629101B2

(12) United States Patent
Pessi et al.

(10) Patent No.: US 8,629,101 B2
(45) Date of Patent: Jan. 14, 2014

(54) CHOLESTEROL DERIVATIVES OF INHIBITORS OF VIRAL FUSION

(75) Inventors: Antonello Pessi, Rome (IT); Elisabetta Bianchi, Rome (IT); Paolo Ingallinella, Rome (IT)

(73) Assignee: Istituto di Ricerche di Biologia Molecolare P. Angeletti S.r.l., Rome (RM) (IT)

( * ) Notice: Subject to any disclaimer, the term of this patent is extended or adjusted under 35 U.S.C. 154(b) by 458 days.

(21) Appl. No.: 12/738,998

(22) PCT Filed: Oct. 20, 2008

(86) PCT No.: PCT/EP2008/064151
§ 371 (c)(1),
(2), (4) Date: Aug. 17, 2010

(87) PCT Pub. No.: WO2009/053339
PCT Pub. Date: Apr. 30, 2009

(65) Prior Publication Data
US 2010/0305028 A1    Dec. 2, 2010

(30) Foreign Application Priority Data

Oct. 22, 2007   (GB) ................................. 0720503.2

(51) Int. Cl.
*A61K 38/16*      (2006.01)
*C07K 14/00*     (2006.01)

(52) U.S. Cl.
USPC ............................................ 514/3.8; 530/324

(58) Field of Classification Search
None
See application file for complete search history.

(56) References Cited

U.S. PATENT DOCUMENTS

| 5,413,999 A | 5/1995 | Vacca et al. |
| 5,646,148 A | 7/1997 | Huff et al. |

FOREIGN PATENT DOCUMENTS

| EP | 0 484 071 A2 | 6/1992 |
| EP | 0 582 455 A1 | 9/1994 |
| WO | WO 2005097199 A1 * | 10/2005 |
| WO | WO 2006105201 A2 * | 10/2006 |

OTHER PUBLICATIONS

Aloia et al., "Lipid Composition and Fluidity of the Human Immunodeficiency Virus", Proc. Natl. Acad. Sci. USA, 1988, 85:900-904.
Aloia et al., "Lipid Composition and Fluidity of the Human Immunodeficiency Virus Envelope and Host Cell Plasma Membranes", Proc. Natl. Acad. Sci. USA, 1993, 90:5181-5185.
Bader et al., "Bioorganic Synthesis of Lipid-Modified Proteins for the Study of Signal Transduction", Nature, 2000, 403:223-226.
Casey, "Protein Lipidation in Cell Signaling", Science, 1995, 268:221-225.
Engelhofer et al., "Ihhibition of Human Ummunodeficiency Virus Type 1 Entry in Cells Expression gp41-Derived Peptides", J. Virol, 2004, 78:568-575.
He et al., "Conserved Residue Lys574 in the Cavity of HIV-1 Gp41 Coiled-coil Domain is Critical for Six-helix Bundle Stability and Virus Entry", J. Biol. Chem., 2007, 282:25631-25639.
Hildinger et al., "Membrane-Anchored Peptide Inhibits Human Immunodeficiency Virus Entry", J. Virol., 2001, 75:3038-3042.
Hovanessian et al., "The Caveolin-1 Binding Domain of HIV-1 Glycoprotein gp41 in an Efficient B Cell Epitope Vaccine Candidate Againts Virus Infection", Immunity, 2004, 21:617-627.
Joyce et al., "Enhancement of alpha-Helicity in the HIV-1 Inhibitory Peptide DP178 Leads to an Increased Affinity for Human Monoclonal Antibody 2F5 but Does Not Elicit Neutralizing Responses in Vitro", J. Biol. Chem., 2002, 277:45811-45820.
Lee et al., "A Nonneutralizing Anti-HIV-1 Antibody Turns into a Neutralizing Antibody When Expressed onthe Surface of HIV-1-Susceptible Cells: A New Way to Fight HIV", J. Immunol., 2004, 173:4618-4626.
Lenz et al., "Trimeric Membrane-Anchored gp41 Inhibits HIV Membrane Fusion", J. Biol. Chem., 2005, 280:4095-4101.
Matthews et al., "Enfuvirtide: The First Therapy to Inhibit the Entry of HIV-1 Into Host CD4 Lymphocytes", Nature Reviews Drug Discovery,2004, 3:215-225.
Moreno et al., "The Membranotropic Regions of the Endo and Ecto Domains of HIV gp41 Envelope Glycoprotein", Biochimica et Biophysica Acta, 2006, 1758:111-123.
Mosier et al. "Highly Potent RANTES Analgues Either Prevent CCR5-Using Human Immunodeficiency Virus Type 1 Infection In Vivo or Raplidly Select for CXCR4-Using Variants", J. Virol, 1999, 73:3544-3550.
Murata et al., "VIP21/caveolin is a cholesterol-binding protein", Proc. Natl. Acad. Sci. USA, 1995, 92:10339-10343.
Ono et al., "Role of Lipid Rafts in Virus Replication", Adv. Virus Res., 2005, 273:5491-5442.
Peisajovich et al., "C-Terminal Octylation Rescues an Inactive T20 Mutant", J. Bio. Chem., 2003, 278:21012-21017.
Peters et al., "The Cholesterol Membrane Anchor of the Hedgehog Protein Confers Stable Membrane Association to Lipid-Modified Proteins", Proc. Natl. Acad. Sci. USA, 2004, 101:8531-8536.
Tanaka Hall et al., "Crystal Structure of a Hedgehog Autoprocessing Domain: Homology between Hedgehog and Self-Splicing Proteins", Cell, 1997, 91:85-97.
Veiga et al., "HIV Fusion Inhibitor Peptide T-1249 is Able to Insert or Adsorb to Lipidic Bilayers, Putative Correlation With Improved Efficiency", J. Am. Chem. Soc., 2004, 1126:14758-14763.
Zeng et al., "Assembly of Synthetic Peptide Vaccines by Chemoselective Ligation of Epitopes: Influence of Different Chemical Linkages and Epitope Orientations on Biological Activity", Vaccine, 2001, 19:3843-3852.

* cited by examiner

*Primary Examiner* — Robert A Wax
*Assistant Examiner* — Jessica Worsham
(74) *Attorney, Agent, or Firm* — Henry P. Wu; Sheldon O. Heber

(57) ABSTRACT

The present invention relates to compounds comprising at least ten contigous amino acids of the HR2 domain of a Type 1 viral fusogenic protein of an enveloped virus, or a derivative thereof, attached at the C-terminal to cholesterol or a derivative thereof; or a pharmaceutically acceptable salt thereof which inhibit viral fusion. Thus compounds of the invention are useful to prevent or treat diseases caused by an enveloped virus.

3 Claims, 7 Drawing Sheets

SEQUENCE LISTING

<160> NUMBER OF SEQ ID NOS: 10

<210> SEQ ID NO 1
<211> LENGTH: 38
<212> TYPE: PRT
<213> ORGANISM: Artificial Sequence
<220> FEATURE:
<223> OTHER INFORMATION: C34 sequence derived from HIV-1 gp41 plus an
      additional C terminal linker sequence of GSGC
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (38)..(38)
<223> OTHER INFORMATION: Cholesterol
<220> FEATURE:
<221> NAME/KEY: MOD_RES
<222> LOCATION: (38)..(38)
<223> OTHER INFORMATION: AMIDATION

<400> SEQUENCE: 1

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Gly Ser Gly Cys
        35

<210> SEQ ID NO 2
<211> LENGTH: 12
<212> TYPE: PRT
<213> ORGANISM: HIV-1
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 2

Glu Leu Leu Glu Leu Asp Lys Trp Ala Ser Leu Trp
1               5                   10

<210> SEQ ID NO 3
<211> LENGTH: 15
<212> TYPE: PRT
<213> ORGANISM: HIV-1

<400> SEQUENCE: 3

Glu Leu Leu Glu Leu Asp Lys Trp Ala Ser Leu Trp Asn Trp Phe
1               5                   10                  15

<210> SEQ ID NO 4
<211> LENGTH: 13
<212> TYPE: PRT
<213> ORGANISM: HIV-1

<400> SEQUENCE: 4

Glu Leu Leu Glu Leu Asp Lys Trp Ala Ser Leu Trp Asn
1               5                   10

<210> SEQ ID NO 5
<211> LENGTH: 34

```
<212> TYPE: PRT
<213> ORGANISM: HIV-1

<400> SEQUENCE: 5

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 6
<211> LENGTH: 38
<212> TYPE: PRT
<213> ORGANISM: Artificial Sequence
<220> FEATURE:
<223> OTHER INFORMATION: N terminal linker sequence of GSGC followed by
      C34 sequence derived from HIV-1 gp41
<220> FEATURE:
<221> NAME/KEY: LIPID
<222> LOCATION: (1)..(1)
<223> OTHER INFORMATION: N-ACYL DIGLYCERIDE N
<220> FEATURE:
<221> NAME/KEY: LIPID
<222> LOCATION: (1)..(1)
<223> OTHER INFORMATION: Cholesterol

<400> SEQUENCE: 6

Cys Gly Ser Gly Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu
        35

<210> SEQ ID NO 7
<211> LENGTH: 38
<212> TYPE: PRT
<213> ORGANISM: Artificial Sequence
<220> FEATURE:
<223> OTHER INFORMATION: C34 sequence derived from HIV-1 gp41 plus an
      additional C terminal linker sequence of GSGK:
<220> FEATURE:
<221> NAME/KEY: LIPID
<222> LOCATION: (38)..(38)
<223> OTHER INFORMATION: PALMITATE

<400> SEQUENCE: 7

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Gly Ser Gly Lys
        35

<210> SEQ ID NO 8
<211> LENGTH: 40
<212> TYPE: PRT
<213> ORGANISM: Artificial Sequence
<220> FEATURE:
<223> OTHER INFORMATION: Peptide T20 i.e. encompassing the MPER of gp41
      plus an additional C terminal linker sequence of GSGC
<220> FEATURE:
<221> NAME/KEY: LIPID
<222> LOCATION: (40)..(40)
<223> OTHER INFORMATION: Cholesterol

<400> SEQUENCE: 8
```

```
Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe Gly Ser Gly Cys
        35                  40

<210> SEQ ID NO 9
<211> LENGTH: 12
<212> TYPE: PRT
<213> ORGANISM: HIV-1

<400> SEQUENCE: 9

Glu Leu Leu Glu Leu Asp Lys Trp Ala Ser Leu Trp
1               5                   10

<210> SEQ ID NO 10
<211> LENGTH: 38
<212> TYPE: PRT
<213> ORGANISM: Artificial Sequence
<220> FEATURE:
<223> OTHER INFORMATION: C34 sequence derived from HIV-1 gp41 plus an
      additional C terminal linker sequence of GSGC
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (38)..(38)
<223> OTHER INFORMATION: AMIDATION
<220> FEATURE:
<221> NAME/KEY: MOD_RES
<222> LOCATION: (38)..(38)
<223> OTHER INFORMATION: Cysteine alkylated with iodoacetamide

<400> SEQUENCE: 10

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Gly Ser Gly Cys
        35
```

CHOLESTEROL DERIVATIVES OF INHIBITORS OF VIRAL FUSION

INCORPORATION-BY-REFERENCE OF SEQUENCE LISTING

A Sequence Listing contained in the ASCII text file named IRTIFD0138USPCT-SEQTXT-2010Apr20.txt, created on Apr. 20, 2010, which is 4,800 bytes, is herein incorporated by reference.

BACKGROUND OF THE INVENTION

The present invention concerns new compounds for inhibiting viral fusion.

"Enveloped viruses", such as orthomyxoviruses, paramyxoviruses, retroviruses, flaviviruses, rhabdoviruses and alphaviruses, are surrounded by a lipid bilayer originating from the host plasma membrane (Ono and Freed, Adv. Virus Res., 2005, 273, 5419-5442). This envelope contains glycoproteins that mediate receptor binding and fusion between viral and host cell membranes. Cholesterol and sphingomyelin are often enriched in these viral lipid bilayers, particularly in lipid-rich rafts in their plasma membrane (Aloia et al, PNAS, 1988, 85, 900-4 and 1993, 90, 5181-5).

In HIV-1 the surface glycoprotein, initially synthesized as a highly glycosylated precursor, gp160, is endoproteolytically cleaved into the surface protein, gp120, that determines the viral tropism through the cellular surface receptors, and the transmembrane protein, gp41, which is responsible for the membrane fusion process (Moreno et al, Biochimica et Biophysica Acta, 2006, 1758, 111-123).

Cholesterol comprises about 30% of the lipid content of the plasma membrane of mammalian cells. Cholesterol and sphingolipids in membranes are often laterally segregated from surrounding glycerolipid-rich bilayers to form membrane microdomains known as "lipid rafts" (P. Casey, Science, 1995, 268, 221-5). A number of transmembrane proteins and receptors, including CD4 which is the primary receptor for HIV envelope gp120, are particularly enriched in lipid rafts. To accomplish the fusion and mixing of cellular and viral contents, gp41 must undergo a complex series of conformational changes apparently triggered by the attachment of gp120 to the CD4 primary receptor and the CCR5 or CXCR4 coreceptors of the target cell.

The completion of co-receptor binding leads to the fusion-active conformation of the viral transmembrane fusion protein gp41. The ectodomain of gp41 contains two heptad repeat regimes: HR1 (proximal to the N terminus) and HR2 (proximal to the C terminus). The hydrophobic fusion peptide region inserts into the host cell membrane, whereas the HR1 region of gp41 form a trimeric coiled coil structure. HR2 regions then fold back within the hydrophobic grooves of the HR1 coiled coil, forming a hairpin structure containing a thermodynamically stable six-helix bundle that draws the viral and cellular membranes together for fusion (Matthews et al, Nature Reviews Drug Discovery, 2004, 3, 215-225).

It has also been shown that gp41 associates with caveolin-1, a structural protein component of a subset of lipid rafts called 'caveolae' (Hovanession et al, Immunity, 2004, 21, 617-627). Caveolin-1 is a cholesterol-binding protein (Murata et al, PNAS, 1995, 92, 10339-10343), so cholesterol is enriched in caveolae, together with HIV-1.

Whatever the precise mechanism, a substantial body of evidence supports the importance of lipid rafts and cholesterol in enveloped virus entry and, for HIV at least, it is generally thought that the lipid rafts on host cell plasma membranes play an essential role in mediating gp120/CD4/coreceptor interactions, while the cholesterol/lipid rafts in HIV viral lipid bilayers are important for maintaining normal structure and function of viral glycoproteins and hence viral infectivity (Ono and Freed, supra).

Proteins containing lipid anchors are commonly found. One type, which has been described recently for Hedgehog proteins, involves a cholesterol molecule esterified to the C-terminal amino acid of a protein following a self-splicing reaction (Tanaka Hall et al, Cell, 1997, 91, 85-97).

The relative ability of lipid anchors to stably localise their associated proteins to lipid membranes has been extensively studied. There is a general relationship between the degree of hydrophobic modification and the stability of membrane insertion: quasi-irreversible binding requires the presence of two long chain anchors in the molecule, for example palmitoyl and farnesyl, or hexadecyl and farnesyl (Barder et al, Nature, 2000, 403, 223-226). By contrast, quasi-irreversible binding is achieved with a single cholesterol moiety (Peters et al, PNAS, 2004, 101, 8531-6). Notably, this modification is effective for a protein (N-Ras) which is normally anchored via a different lipid.

A general advantage of targeting a peptide to a membrane is to effectively increase its concentration over the bulk aqueous phase. This results in augmenting its binding affinity toward membrane-bound receptors.

For antiviral agents, including peptides, proteins, and antibodies, which target fusion as mechanism of action, a number of examples document the advantage of anchoring the inhibitor to a membrane. For HIV in particular, a construct, including the fusion inhibitor T20 (enfuvirtide, FUZEON®) (Matthews et al, supra), a short linker and a transmembrane (TM) domain, was a much more powerful inhibitor than the same construct lacking the TM domain (Egelhofer et al, J. Virol., 2004, 78, 568-575). Importantly, mutations in the Trp-rich region which completely inactivated the free peptide, did not reduce the potency of the membrane-anchored one (Hildinger et al, J. Virol., 2001, 75, 3038-3042). Similarly a construct including the TM domain of gp41 and the entire C-terminal heptad repeat HR2 incorporated into liposomes had potent antiviral activity (Lenz et al, J. Biol Chem., 2004, 280, 4095-4101).

Addition of a C-terminal octyl group to the fusion inhibitor T20 induced a significant increase in its inhibitory potency. Furthermore, octylation could rescue the activity of an otherwise inactive mutant, in which the C-terminal residues GNWF were replaced by ANAA. The mutant with a C-terminal octyl group showed potency similar to that of the wild type T20. Importantly, the position of the octyl group was critical, since N-terminal derivatization had no effect on antiviral potency (Peisajovich et al, J. Biol. Chem., 2003, 278, 21012-7). An increased ability to partition into membranes has been recently proposed as the reason behind the increased clinical efficacy of the $2^{nd}$-generation inhibitor T1249 when compared with T20 (Veiga et al, J. Am. Chem. Soc, 2004, 126, 14758-63).

N-terminal extension of the chemokine RANTES, a natural ligand of the HIV co-receptor CCR5, with a hydrophobic group, has been used to greatly increase antiviral potency. Both the hydrophobicity and the chemical nature of the connection with the protein were important for maximal potency (Mosier et al, 1999, J. Viral, 1999, 73, 3544-50).

It has also been shown that when a bona fide non-neutralizing antibody, which did not inhibit HIV-1 entry when produced as a soluble protein, was anchored to the cell surface of target cell by fusion with a transmembrane anchoring domain, it acted as a neutralizing antibody (Lee et al, J. Immunol., 2004, 173, 4618-26).

SUMMARY OF THE INVENTION

In view of the above background and analysis, the present inventors proposed attaching a cholesterol moiety as a lipid anchor to peptide inhibitors derived from viral fusogenic proteins. To that end cholesterol anchored HIV viral fusion inhibitors have been made which are many times more potent than any HIV fusion inhibitors previously known.

Thus the present invention provides an inhibitor of viral fusion comprising at least ten contigous amino acids of the HR2 domain of a Type 1 viral fusogen protein of an enveloped virus, or a derivative thereof, attached at the C-terminal to cholesterol or a derivative thereof or a pharmaceutically acceptable salt thereof.

For example, the enveloped virus may be an orthomyxovirus, paramyxovirus, retrovirus, flavivirus, rhabdovirus or alphavirus. It is believed that viral fusion in all these viruses occurs in a manner analogous to the mechanism of viral fusion in HIV-1.

Thus each of these viruses has an equivalent to the HR2 domain gp41 of HIV-1 which is involved in viral fusion and can be inhibited in a manner analogous to the inhibition of HIV-1 viral fusion demonstrated herein. A preferred enveloped virus is human immunodeficiency virus 1 (HIV-1).

The inhibitor preferably comprises at least fifteen contiguous acids, and more preferably at least twenty-five contiguous amino acids, for example more than thirty contiguous amino acids, of the HR2 domain. There may be additional natural or synthetic amino acids present in the fusogenic protein portion of the inhibitor.

In particular, the HR2 domain in HIV-1 is found in viral protein gp41. Using the Glade B consensus numbering of Moreno et al, Biochimica et Biophysia Acta, 2006, 1758, 111-123, an especially preferred contiguous series of amino acids is 628-661 of gp41 of HIV-1, also known as C34. The HR2 domain of gp41 extends from amino acids 620-663 and any contiguous sequence of at least ten amino acids from this domain may be used in the present invention.

The C-terminus of the fusogenic protein may be a carboxy terminus or it may alternatively be a carboxamide, or a $C_{1-6}$alkyl ester optionally substituted by halogen.

The fusogenic protein may be directly bound to cholesterol, or a derivative thereof. Alternatively, they may be connected by a linker which comprises two or more amino acids. The amino acids may be naturally occurring or synthetic. The benefit of a linker is that it assists relative movement between the fusogenic protein and the cholesterol or derivative thereof which facilitates presenting the fusogenic protein in the correct orientation for incorporation into the HR2 helix and so to disrupt viral fusion, as further described below:

Thus, the linker may comprise $(Gly)_{n+1}$, $(GlySerGly)_n$ or $(Gly-Pro)_n$ where n is 1 or greater, for example, 1 to 12, 1 to 6 or 1 to 4. GlySerGly is one example of a sequence of amino acids which may form part of a linker.

The linker may further comprise a moiety —$(OCH_2CH_2)_m$— where m is from 1 to 15, for example 2 to 10, 2 to 6 or 4. Introduction of a (poly)ethyleneglycol group assists solublity in aqueous media.

The final amino acid of the linker is preferably cysteine. It is generally convenient to utilise the sulphur atom of cysteine to form a thioether bond with the non-amino acid portion of the linker which is then attached to the cholesterol or derivative thereof.

The sulphur atom of the cysteine residue may be connected to the (poly)ethyleneglycol group by an amide moiety such as —$C_{1-4}$alkylene C(O)NH— or —$C_{1-4}$alkylene C(O)NHC$_{1-4}$alkylene-such as —$CH_2C(O)NHCH_2CH_2$—.

The linker may be connected to any convenient position on the cholesterol or derivative thereof. In particular, connection may be via the hydroxy group of the cholesterol. Thus the linker may be connected to the cholesterol by a group —C(O)— or —$C_{1-4}$alkylene C(O)—, such as —$CH_2C(O)$—.

Examples of the non-amino acid portion of the linker are —$CH_2C(O)$— and —$CH_2C(O)NHCH_2CH_2(OCH_2CH_2)_4C(O)$—. The amino acid portion of such linkers may be Gly-SerGlyCys where the cystene is attached to the rest of the linker via a thioether bond.

It will be appreciated that numerous alterations can be made to the linker which will not affect the essential activity of the viral infusion inhibitor and such alterations fall within the scope of the present invention.

Particularly preferred embodiments of the invention are:

SEQ ID NO. 1

Ac-WMEWDREINNYTSLIHSLIEESQNQQEKNEQELLGSG

; and

SEQ ID NO. 1

Ac-WMEWDREINNYTSLIHSLIEESQNQQEKNEQELLGSG and the pharmaceutically acceptable salts thereof.

A particular advantage conferred by the cholesterol moiety is that it increases the local concentration of the peptide portion of the molecule in the cellular component (in this case lipid rafts in the host cell plasma membrane) where viral and host cell fusion take place. In addition, the cholesterol group improves the pharmacokinetic properties of the antiviral peptide.

Thus the present invention also provides pharmaceutical composition comprising an inhibitor of viral fusion, as described above, and a pharmaceutically acceptable excipient. In one embodiment the pharmaceutical composition is a pessary. In another embodiment it is a vaginal ring. In a further embodiment it is a cream or gel suitable for vaginal application.

There is also provided an inhibitor of viral fusion as described above, for use in a method of treatment of the human body by therapy or prophylaxis. The method may be the prevention or treatment of infection by an enveloped virus, such as HIV-1 infection, or the development of AIDS.

Thus, there is provided the use of an inhibitor of viral fusion as described above, for the manufacture of a medicament for preventing or treating an infection by an enveloped virus, such as HIV-1, or for treating AIDS.

The invention also provides a method of treating a subject prone to or suffering from infection by an enveloped virus which comprises administering to that subject a prophylactically or therapeutically effective amount of an inhibitor of viral fusion as defined above. In one embodiment the method is for the prevention or treatment of infection by HIV-1. In a further embodiment it is a method of treatment of AIDS.

The invention also provides a combination of an inhibitor of viral fusion, as defined above, and another compound known to treat or prevent infection by an enveloped virus, such as HIV-1, for separate, simultaneous or sequential administration.

DETAILED DESCRIPTION OF THE INVENTION

Figure 1:
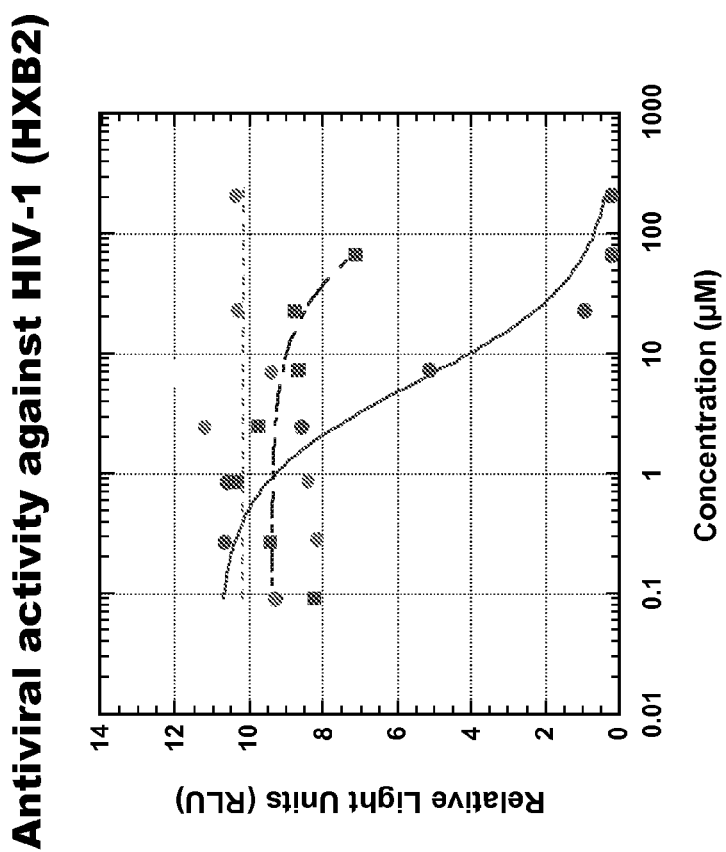
FIG. 1 shows antiviral activity against HIV-1 (HXB2) of a peptide from the membrane-proximal external region (MPER) of HIVgp41 with two lipid anchors, a Cys(cholesterol) group and a bis-Lys($N^\epsilon$-Palmitoyl) group, plus a control peptide where the C-terminal cysteine is derivatized with iodoacetamide. The β-aa peptide Ac-ELLELDKWASLW-NH$_2$ (SEQ ID NO.2) encompasses the epitope of MAb2F5.
Figure 1:
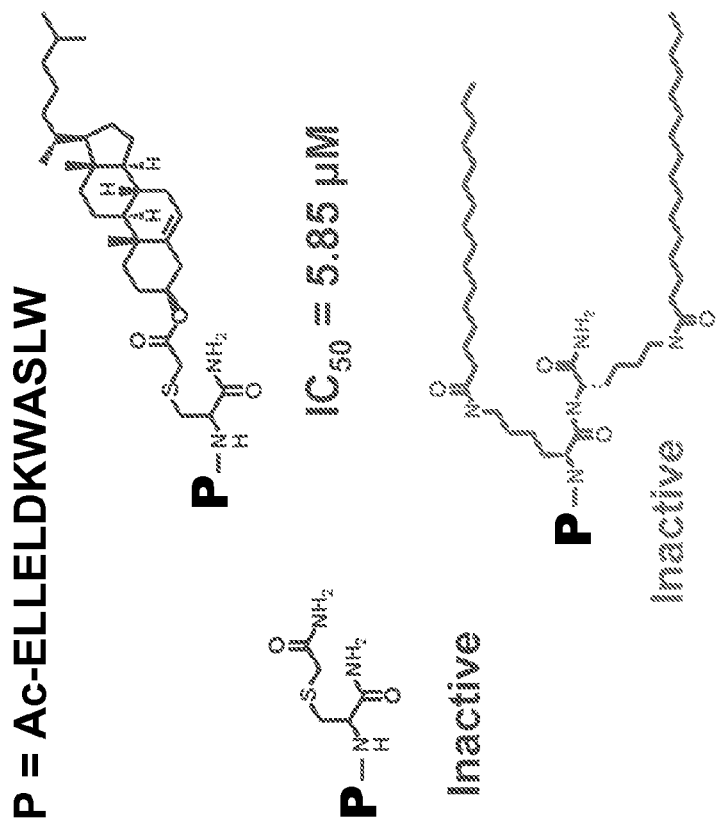

In addition to primates, such as humans, a variety of other mammals can be treated according to the method of the present invention. For instance, mammals including, but not limited to, cows, sheep, goats, horses, dogs, cats, guinea pigs, rats, or other bovine, equine, canine, feline, rodent or murine species can be treated. However, the method can also be practiced in other species such as avian species (e.g., chickens) or fish.

Thus, the present invention may be used to prevent or treat diseases caused by enveloped viruses such as orthomyxoviruses, paramyxoviruses, retroviruses, flaviviruses, rhabdoviruses or alphaviruses. Thus diseases that may be prevented or treated include: influenza caused by influenza A, B or C viruses or by parainfluenza virus 1-4 or by respiratory syncytial virus; mumps; measles; canine distemper virus; HIV-1 associated myelopathy, Strongyloides stercoralis hyper infection and adult T-cell leukaemia/lymphoma caused by human T-cell lymphotropic virus 1, myelopathy/tropical spastic paraparesis—like neurological disease caused by human T-cell lymphotropic virus II, bovine leukaemia caused by bovine leukaemia virus; sarcomas, tumours and anaemia caused by alpharetroviruses such as Rous sarcoma virus, avian leucosis virus or avian myeloblastosis virus; mouse breast cancer caused by mouse mammary tumour virus; sarcomas and leukaemias caused by gammaretroviruses such as murine leukaemia virus, feline leukaemia virus, feline sarcoma virus and reticuloendotheliosis viruses; tumours and sarcomas caused by epsilonretroviruses such as Walleye dermal sarcoma virus and Walleye epidermal hyperplasia virus 1 and 2; immune deficiency diseases caused by lentiviruses such as bovine immunodeficiency virus, HIV-1, HIV-2, simian immunodeficiency virus, feline immunodeficiency virus and swamp fever caused by equine infectious anaemia virus; yellow fever; hepatitis C; bovine diarrhoea caused by bovine diarrhoea virus 1; tick-borne diseases such as Kyasanur forest disease, Omsk haemorrhagic fever, Powassan encephalitis, tick-borne encephalitis and louping-ill; dengue haemorrhagic fever; Japanese encephalitis; Murray Valley encephalitis; St Louis encephalitis; West Nile fever, meningitis and encephalitis; Classic Swine Fever; bovine ephemeral fever; rabies; Semliki Forest disease; O' nyong'nyong; Chikungunya; Ross River fever; Eastern equine encephalitis; Western equine encephalitis and Venezuelan equine encephalitis; and mayaro.

The present invention is further directed to the use of these compounds in the prevention or treatment of infection by a retrovirus, in particular a lentivirus such as human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The term "subject," (alternatively referred to herein as "patient") as used herein refers to an animal, preferably a mammal, most preferably a human, who has been the object of treatment, observation or experiment.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the antiviral agents, immunomodulators, anti-infectives, or vaccines suitable for treating HIV infection and AIDS, and known to those of ordinary skill in the art, including those listed in the following Table:

| Drug Name | Manufacturer | Indication |
|---|---|---|
| ANTIVIRALS | | |
| Amprenavir<br>141 W94<br>GW 141 | Glaxo Wellcome | HIV infection, AIDS,<br>ARC<br>(protease inhibitor) |
| Abacavir<br>GW 1592<br>1592U89 | Glaxo Welcome | HIV infection, AIDS,<br>ARC<br>(reverse transcriptase inhibitor) |
| Acemannan | Carrington Labs<br>(Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen<br>(Los Angeles, CA) | ARC, PGL, HIV positive, AIDS |
| Alpha Interferon | Glaxo Wellcome | Kaposi's sarcoma, HIV, in combination w/Retrovir |
| Ansamycin<br>LM 427 | Adria Laboratories<br>(Dublin, OH)<br>Erbamont<br>(Stamford, CT) | ARC |
| Antibody which neutralizes pH labile alpha aberrant Interferon | Advanced Biotherapy Concepts<br>(Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623<br>(CGP-73547) | Bristol-Myers Squibb/<br>Novartis | HIV infection, AIDS,<br>ARC<br>(protease inhibitor) |
| BMS-234475<br>(CGP-61755) | Bristol-Myers Squibb/<br>Novartis | HIV infection, AIDS,<br>ARC<br>(protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| CYTOVENE ®<br>Ganciclovir | Syntex | sight threatening CMV peripheral CMV retinitis |
| Delaviridine | Pharmacia-Upjohn | HIV infection, AIDS,<br>ARC<br>(protease inhibitor) |
| Dextran Sulfate | Ueno Fine Chem.<br>Ind. Ltd. (Osaka, Japan) | AIDS, ARC, HIV positive asymptomatic |
| ddC<br>Dideoxycytidine | Hoffman-La Roche | HIV infection, AIDS, ARC |
| ddI<br>Dideoxyinosine | Bristol-Myers Squibb | HIV infection, AIDS, ARC; combination with AZT/d4T |
| mozenavir<br>(DMP-450) | AVID<br>(Camden, NJ) | HIV infection, AIDS,<br>ARC<br>(protease inhibitor) |
| EL10 | Elan Corp, PLC<br>(Gainesville, GA) | HIV infection |
| Efavirenz<br>(DMP 266)<br>(−) 6-Chloro-4(S)-cyclopropylethynyl-<br>4(S)-trifluoro-methyl-<br>1,4-dihydro-2H-3,1-benzoxazin-2-one, | DuPont (SUSTIVA ®),<br>Merck (STOCRIN ®) | HIV infection, AIDS,<br>ARC<br>(non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |

-continued

| Drug Name | Manufacturer | Indication |
|---|---|---|
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| Enfuvirtide | Roche/Trimen's | HIV infection |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV Infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir (ABT-538) | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| VIRAZOLE ® Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma in combination with other therapies (reverse transcriptase inhibitor) |
| ABT-378; Lopinavir | Abbott | HIV infection, AIDS, ARC (protease inhibitor) |
| ABT-378/r; contains lopinavir and ritonavir; KALETRA ® | Abbott | HIV infection, AIDS, ARC (protease inhibitor) |
| JE2147/AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infection, AIDS, ARC (fusion inhibitor) |
| atazanavir (BMS 232632) | Bristol-Myers-Squibb | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |

-continued

| Drug Name | Manufacturer | Indication |
|---|---|---|
| DPC 681 & DPC 684 | DuPont | HIV infection, AIDS, ARC (protease inhibitors) |
| DPC 961 & DPC 083 | DuPont | HIV infection AIDS, ARC (nonnucleoside reverse transcriptase inhibitors) |
| TRIZIVIR ® (contains abacavir, lamivudine, and zidovudine) | GlaxoSmithKline | HIV infection, AIDS, ARC (reverse transcriptase inhibitors) |
| tipranavir (PNU-140690) | Boehringer Ingelheim (purchased from Pharmacia & Upjohn) | HIV infection, AIDS, ARC (protease inhibitor) |
| tenofovir disoproxil fumarate | Gilead | HIV infection, AIDS, ARC (reverse transcriptase inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| REMUNE ™ (inactivated Zairian HIV-1 strain HZ-321 | Immune Response Corp. | immunotherapeutic |
| rCD4 Recombinant Soluble Human CD4 | Genentech | AIDS, ARC |

-continued

| Drug Name | Manufacturer | Indication |
|---|---|---|
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (ENBREL ®) | rheumatoid arthritis |
| infliximab | Centocor (REMICADE ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine isethionate for inhalation | Fisons Corporation | PCP prophylaxis |
| Spiramycin Intraconazole-R51211 | Rhone-Poulenc Janssen Pharm. | cryptosporidia diarrhea histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of the compounds of this invention with HIV/AIDS antivirals, immunomodulators, anti-infectives or vaccines is not limited to the list in the above Table, but includes in principle any combination with any pharmaceutical composition useful for the treatment of HIV infection or AIDS. When employed in combination with the compounds of the invention, the HIV/AIDS antivirals and other agents are typically employed in their conventional dosage ranges and regimens as reported in the art, including the dosages described in the *Physicians' Desk Reference, 54th* edition, Medical Economics Company, 2000. The dosage ranges for a compound of the invention in these combinations are the same as those set forth above just before the above Table.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-34(S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)—N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)—N'-(t-butyl-carbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclo propylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)—N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

One favoured combination when the enveloped virus is HIV-1, is with enfurvirtide which is administered in a dose of from 60 to 400 mg daily, for example 90 mg twice daily. Enfurvirtide may be given orally as a tablet or injected subcutaneously as a 1.0 ml injection.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration or pessaries, rings, creams or gels for vaginal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions caused by enveloped viruses an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral, vaginal or rectal administration, the compositions are preferably provided in the form of tablets; pessaries, rings, gels or creams; or suppositories containing 1.0 to 1000 milligrams of the active ingredient per unit dose, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Supporting Examples

Lipid-anchored peptides derived from the membrane-proximal external region (MPER) of gp41.

Figure 2:
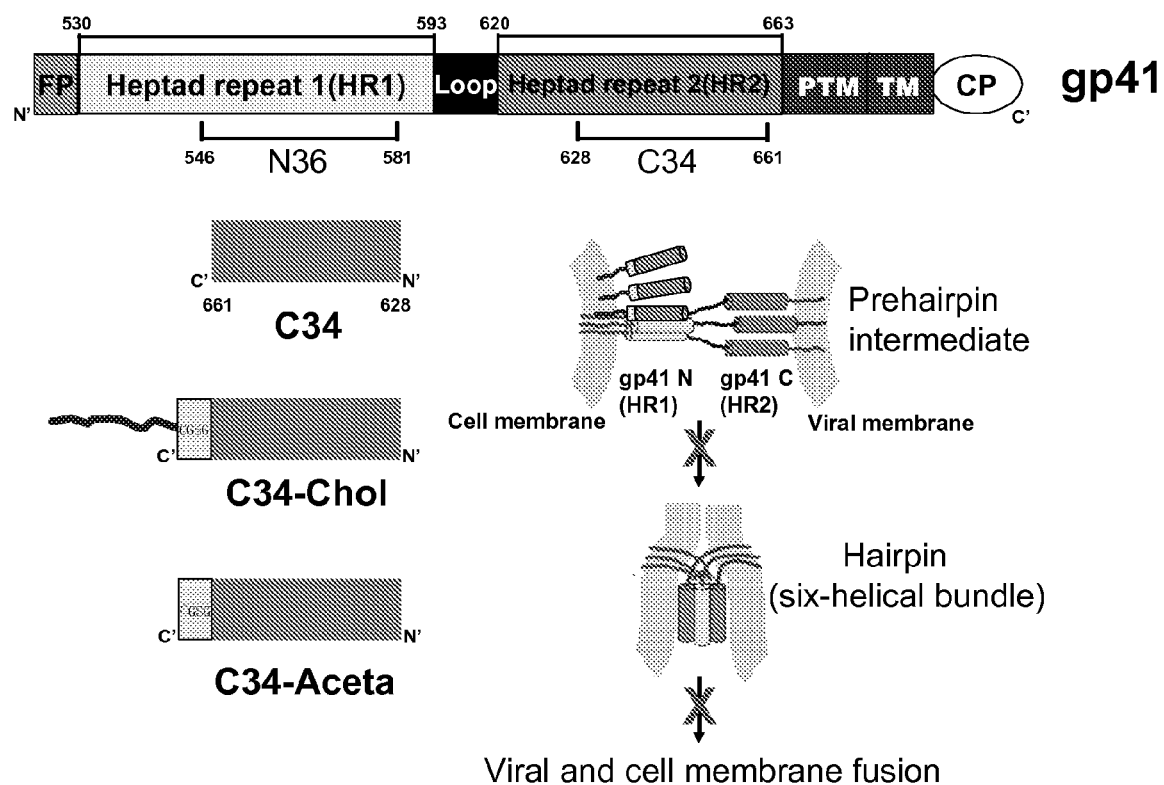
FIG. 2 shows the currently accepted model for HIV fusion and for the mechanism of action of HR2 (C-domain) peptides. The Figure shows C34-chol bound to the host cell membrane in an antiparallel orientation to the HR1 (N-peptide) domain.

The antiviral activity of a peptide from the membrane-proximal external region (MPER) of gp41, which also includes the epitope of monoclonal antibody (MAb) 2F5, ELLELDKWASLWNWF (SEQ ID NO.3) ($IC_{50}$=30 µM) was greatly diminished by deletion of the last two C-terminal amino acids: ELLELDKWASLWN (SEQ ID NO.4) ($IC_{50}$>100 µM), in agreement with the need for the peptide to partition into the membrane to exert its antiviral activity. Accordingly, when peptide ELLELDKWASLW (SEQ ID NO.9) ($IC_{50}$>100 μM) was derivatized with a C-terminal cholesterol group, it regained antiviral potency (IC50 =5.85 μM): the cholesterol group boosted activity more than the natural three-amino acid C-terminal NWF extension. Moreover, the nature of the lipid was important, since a bis-Lys ($N^{\epsilon}$-Palmitoyl) group was ineffective. The antiviral activity against HIV-I (HXB2) for some of these compounds is shown in FIG. 1. Details of the assay used can be found in Joyce et al, J. Biol Chem., 2002, 277, 45811-45820.

Lipid-anchored peptides derived from the C-terminal heptad repeat domain of Gp41. Peptides derived from the C-terminal heptad repeat region of gp41 are potent inhibitors of viral infectivity. Peptide T20, also known as DP-178 and now commercially as enfuvirtide/FUZEON®, is used in the clinic for the treatment of therapy-experienced AIDS patients. T20 encompasses the MPER of gp41, thus being endowed with certain affinity for membranes. By contrast, C34 does not show any membrane tropism per se. A derivative of C34 (C34-chol) was prepared with a cholesterol group attached, via a thioether bond, to the side chain of a cysteine residue added to the C-terminus. To allow for flexibility between the lipid anchor and the C34 sequence, a Gly-Ser-Gly spacer was inserted between the two. Importantly, the current model for HIV fusion indicates the need for an antiparallel arrangement of the N- and C-domain peptides (C34 is derived from the latter), and dictates that the position of a membrane anchor should be at the C-terminus of C34: N-terminal derivatization would interfere with binding to the N-peptide. FIG. 2 shows the current model for HIV fusion and the mechanism of action (MOA) of C-peptides. The figure makes immediately clear why, according to this model, the lipid anchor should be at the C-terminus of the inhibitor.

Table 1 shows the sequence of C34-chol and all the control peptides, while Table 2 shows their antiviral activity in the single-cycle infectivity assay (VERTICAL).

TABLE 1

Sequence of C34-chol and controls.

| Peptide | Sequence[1] |
|---|---|
| C34 | WMEWDREINNYTSLIHSLIEESQNQQEKNEQELL (SEQ ID NO. 5) |
| C34-Chol | WMEWDREINNYTSLIHSLIEESQNQQEKNEQELLGSGC (Chol) (SEQ ID NO. 1) |
| C34-Aceta | WMEWDREINNYTSLIHSLIEESQNQQEKNEQELLGSGC (Aceta) (SEQ ID NO. 10) |
| Chol-C34 | C(Chol)GSG WMEWDREINNYTSLIHSLIEESQNQQEKNEQELL (SEQ ID NO. 6) |
| C34-Pam | WMEWDREINNYTSLIHSLIEESQNQQEKNEQELLGSGK (Pam) (SEQ ID NO. 7) |
| T20-Chol | YTSLIHSLIEESQNQQEKNEQELLELDKWASLWNWF-GSG-C(Chol) (SEQ ID NO. 8) |

[1]Chol, cholesterol; C(Aceta), cysteine alkylated with iodoacetamide; K(Pam), Lys(N$^\epsilon$-palmitoyl)

Antiviral potency of peptides derived from the C-terminal heptad repeat domain of gp41. Addition of cholesterol to C34 increases its antiviral potency 50-fold over C34 and the control peptide C34-Aceta, where the cysteine residue is alkylated with iodoacetamide. As expected, addition of cholesterol at the N-terminus instead of the C-terminus is detrimental to antiviral activity (50-fold decrease compared to underivatized C34). Also as expected, cholesterol is a much better lipid anchor than palmitic acid, since C34-Pam has comparable activity to underivatized C34. Finally, addition of cholesterol is detrimental to T20, perhaps as a result of interference with its own lipophilic sequence, or because of a different MOA (25).

Overall, C34-chol is ~100-fold more potent than marketed fusion inhibitor enfuvirtide/FUZEON®, and is the most potent HIV inhibitor known to date.

TABLE 2

Antiviral potency of C34-chol and controls. The antiviral potency of the peptides was determined in a single-cycle infectivity assay against HIV-HXB2. All data were from three independent experiments and expressed as mean ± SEM

| Peptide | IC$_{50}$ viral infectivity (pM) |
|---|---|
| C34 | 205 ± 59 |
| C34-Aceta | 270 ± 88 |
| C34-Chol | 4 ± 1 |

TABLE 2-continued

Antiviral potency of C34-chol and controls. The antiviral potency of the peptides was determined in a single-cycle infectivity assay against HIV-HXB2. All data were from three independent experiments and expressed as mean ± SEM

| Peptide | IC$_{50}$ viral infectivity (pM) |
|---|---|
| Chol-C34 | 9515 ± 3172 |
| C34-Pam | 713 ± 305 |
| T20 | 692 ± 245 |
| T20-Chol | 3726 ± 1196 |

Figure 7:
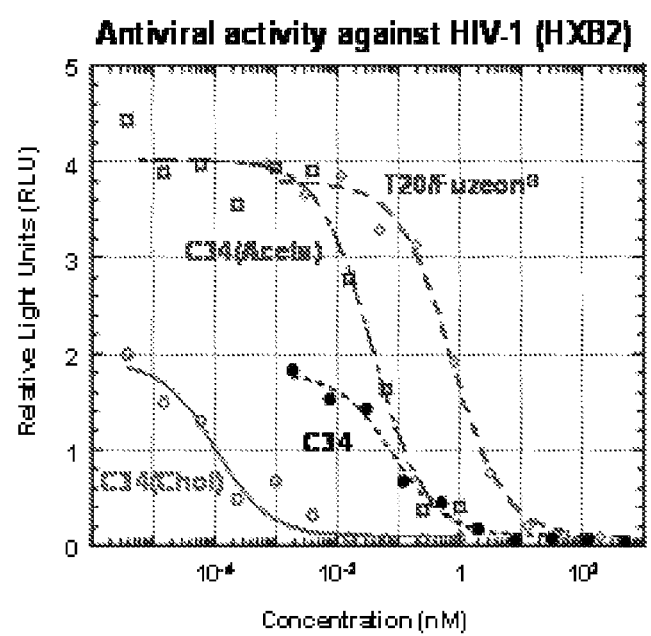
FIG. 7 shows antiviral activity agent HIV-1 (HXB2) of C34-chol, C34 (aceta), C34 and T20/FUZEON®.

Some of the results are also shown in FIG. 7.

Breadth of the antiviral response of C34-chol. When tested on a variety of viral strains, C34-chol showed widespread response with comparable IC$_{50}$ in all strains. Across the whole panel, C34-chol was ~50-fold more potent than underivatized or cys-alkylated C34.

TABLE 3

Antiviral potency of C34-chol and controls against multiple HIV-1 isolates. The antiviral potency of the peptides against multiple HIV-1 isolates was determined in a single-cycle infectivity assay. All data were from three independent experiments and expressed as mean ± SEM. VSVG is a control virus with no HIV envelope.

| | IC$_{50}$ Viral infectivity (pM)[1] | | |
|---|---|---|---|
| HIV isolate | C34-chol | C34-Aceta | C34 |
| HXB2 | 8 ± 2 | 227 ± 104 | 141 ± 59 |
| BAL | 9 ± 5 | 344 ± 82 | 273 ± 75 |
| NL4-3 | 6 ± 2 | 173 ± 20 | 292 ± 67 |
| MN-1 | 21 ± 11 | 1003 ± 184 | 866 ± 367 |
| 89.6 | 34 ± 12 | 6022 ± 480 | 3912 ± 1429 |
| R8 | 15 ± 8 | 516 ± 119 | 314 ± 35 |
| SHIVsf162p3 | 9 ± 5 | 1271 ± 301 | 694 ± 353 |
| VSVG | NA | NA | NA |

NA, not active

Accumulation of C34-chol to the target cell membrane is key to its MOA. To confirm that accumulation of the peptide to the site of action is key to the MOA of C34-chol, an experiment was performed where the peptide and its controls were incubated with P4-2/R5 cells at 37° C. for 1 h, followed by thorough washing to remove unbound peptide, and by addition of HIV-HXB2 to initiate infection.

TABLE 4

Antiviral potency of C34-chol is retained when pre-incubated with target cells followed by thorough wash. Antiviral potency with/without wash was determined as before. Data shown are from a single experiment, representative of three repeats.

| | IC$_{50}$ Viral infectivity (pM) | | |
|---|---|---|---|
| Peptide | No wash | With wash | IC$_{50}$ fold change |
| C34-chol | 7 | 50 | 7 |
| C34-Aceta | 194 | 109,610 | 565 |
| C34 | 313 | 116,930 | 374 |

While the antiviral potency of underivatized and cys-alkylated C34 was decreased ~500-fold, C34-chol only lost 7-fold.

Figure 3:
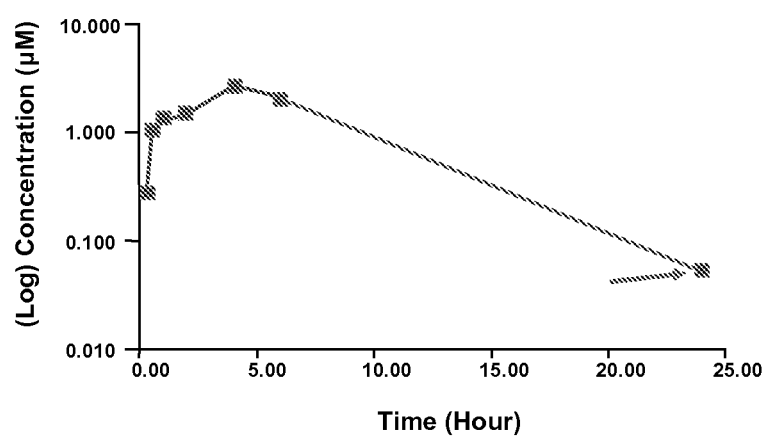
FIG. 3 shows the PK of C34-cholesterol (PEP2675) given ip to mouse at 3.5 mg/k.

Effect of lipid derivatization on the pharmacokinetic properties of C34-chol. In addition to providing improved antiviral potency, derivatization with cholesterol also extends the half-life of the peptide in vivo. When injected intraperitoneally into the mouse at the concentration of 3.5 mg/kg, a plasma concentration of ~60 nM of C34-chol was still detectable after 24 h: this concentration is still >500-fold the measured IC$_{50}$ (7 pM) in the single-cycle infectivity assay, as shown in FIG. 3. The results obtained were: C$_{max}$ 3.1 µM, T$_{max}$ 4 h, Cl/F 0.60 ml/min/kg, AUC$_{(0-6h)}$ 11.5 µMh.

Experimental Details (Methods)

HIV-1 Infectivity Assay (31). P4-2/R5 cells (HeLa cells expressing endogenous CXCR4 and stably transfected to express CD4 and CCR5 which also contain an integrated β-galactosidase reporter gene under control of an HIV LTR promoter) maintained in phenol red-free Dulbecco's modified Eagle's medium, 10% fetal bovine serum, 1% penicillin/streptomycin were seeded in 96-well plates at 2.5×10$^3$ cells/well and infected the following day with the HXB2 strain (and a variety of other strains in some cases) of HIV-1 (Advanced Biotechnology Inc., Bethesda, Md.) in the presence of titrations of the test inhibitory peptides at 37° C. After 48 h incubation with both virus and inhibitory peptides, cells were lysed and β-galactosidase was detected using Gal Screen™ chemiluminescent substrate (Applied Biosystems, Foster City, Calif.) according to the manufacturer's instructions. Data were obtained using a Dynex luminometer and IC$_{50}$ values were calculated by KaleidaGraph. Although agents that block any step of the early HIV life cycle including entry, reverse transcription, integration, and tat-mediated transcription can all inhibit production of β-galactosidase, C34-derived peptides are considered to act specifically at a pre-entry step by binding to HIV-1 envelope extracellularly and thus inhibiting viral entry into the host cell.

In one set of experiment where the retention and functioning of three peptides (C34-Chol, C34-Aceta, and C34) on target cell surface was evaluated, each peptide with proper serial dilution was pre-incubated with P4-2/R5 cells at 37° C. for 1 h, followed by three washes with culture medium to remove unbound peptides (no wash as control) and addition of HXB2 to initiate infection. After 48 h, the antiviral activities of the residual peptides that survive the washing steps were determined by measuring the f3-galactosidase activities within lysed cells as described above.

Synthesis of cholesterol-derivatized peptides. The cholesterol moiety is generally attached to the peptide via a thioether linkage with the thiol group of an extra cysteine residue, added C-terminally to the gp41 sequence.

For both series of peptides, a thioether bond is generally used as an attachment point, since it provides both for non hydrolyzable anchoring to the membrane, and for an easy preparation of the vaccine via chemoselective methods. Chemoselective reaction between bromoacetyl groups and free thiols are described in Zeng et al, Vaccine, 2001, 19, 3843-3852.

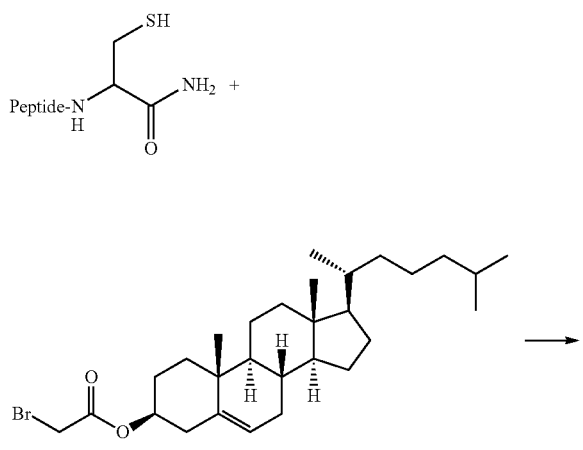

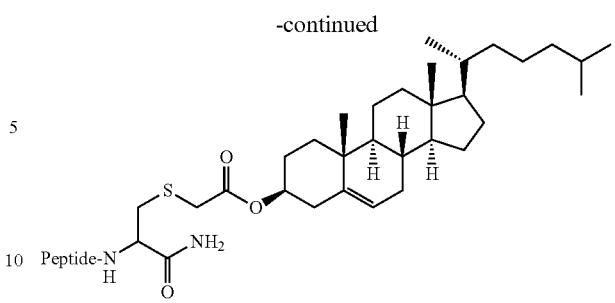

Bromoacetyl compounds can be made as described in the Examples, or by analogy, thereto, by using commercially available compounds or by well known methods from commercially available compounds.

Methods of making peptides are well known in the art. Synthetic or microbiological methods can be used.

Derivatives of cholesterol are commercially available or can be made from commercially available materials by well known methods.

The following methods illustrate the present invention.

REFERENCE EXAMPLE 1

Synthesis of Bromoacetyl-Cholesterol

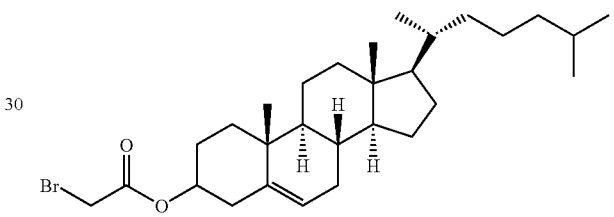

A mixture of 100 mg of cholesterol and 40 mg of bromoacetic acid (1.1 eq) was dissolved in 10 mL of anhydrous dichloromethane. Then 44 µl (1.1 eq) of DIPC(N,N-diisopropylcarbodiimide) and 1.5 mg (0.05 eq) of DMAP (4-dimethylaminopyridine) were added. The solution was left stirring at room temperature for 48 h and analyzed by TLC using a mixture of n-hexane/EtOAc 10/1 as solvent systems. The solvent was evaporated and the reaction product was purified by silica gel flash chromatography in n-hexane/dichloromethane 1/1. The fractions containing the product were pooled, evaporated and then lyophilized in water/acetonitrile 20/80. The purified product was analyzed by NMR. Yield: 73%.

REFERENCE EXAMPLE 2

Synthesis of PEP2667

Ac-WMEWDREINNYTSLIHSLIEESQN-QQEKNEQELLGSGC-NH$_2$ (SEQ ID NO.1)

Peptide PEP2667 was prepared by standard Solid-phase Peptide Synthesis, using Fmoc/t-Bu chemistry on a Pioneer Peptide Synthesizer (Applied Biosystems). To produce the peptide C-terminal amide, the peptide was synthesized on a Champion PEG-PS resin (Biosearch Technologies, Inc., Novato, Calif.) that had been previously derivatized with the Fmoc-Rink linker using DIPCDI/HOBt as activators. All the acylation reactions were performed for 60 min with 4-fold excess of activated amino acid over the resin free amino groups. Amino acids were activated with equimolar amounts of HBTU (2-(1H-benzotriazole-1-yl)-1,1,3,3-tetramethyluronium hexafluorophosphate) and a 2-fold molar excess of DIEA (N,N-diisopropyl-ethylamine). The side chain protecting groups were: tert-butyl for Asp, Glu, Ser, Thr and Tyr; trityl for Asn, Cys, Gln and His; tert-butoxy-carbonyl for Lys, Trp; and 2,2,4,6,7-pentamethyldihydrobenzofuran-5-sulfonyl for Arg.

Figure 4:
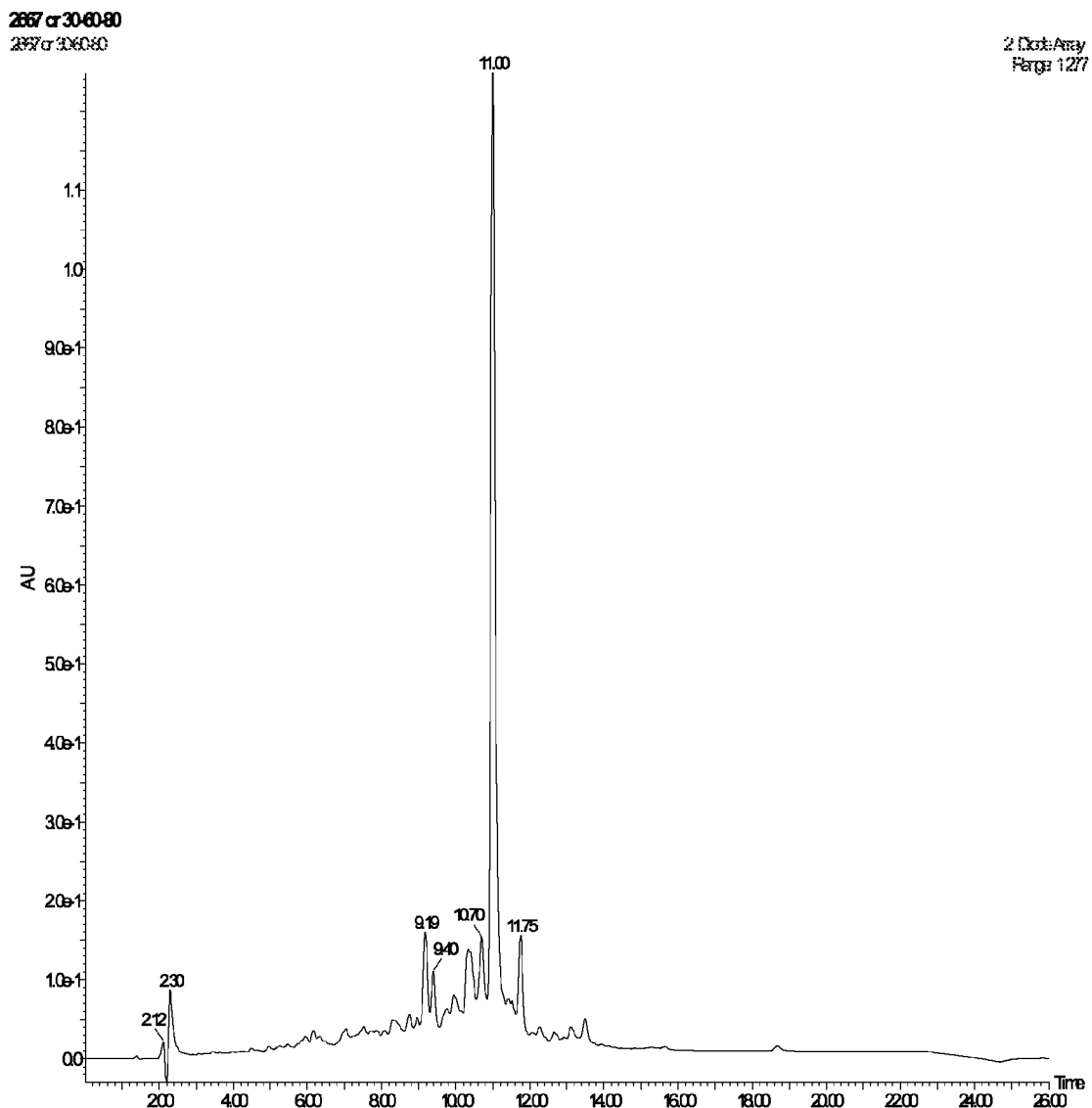
FIG. 4 shows the HPLC trace of crude PEP2667 (the amino acid precursor to PEP2675) after cleavage and lyophilisation.

At the end of the assembly, the dry peptide-resin was treated with 82.5% TFA, 5% phenol, 5% water, 5% thioanisole, 2.5% ethanedithiol for 1.5 h at room temperature. The resin was filtered and the solution was evaporated and the peptide pellet treated several times with diethylether to remove the organic scavengers. The final pellet was dried, resuspended in 1:1 (v/v) H$_2$O: acetonitrile and lyophilized. The crude peptide was analyzed by liquid chromatography-mass spectrometry using a Waters-Micromass LCZ Platform with a Phenomenex, Jupiter C$_4$ column (150×4.6 mm, 5 μm) using as eluents (A) 0.1% TFA in water and (B) 0.1% TFA in acetonitrile, and the following linear gradient: 30% (B)-60% (B) in 20'-80% (B) in 3'-80% (B) for 3', flow 1 ml/min. The crude peptide was dissolved at 1 mg/ml in 70% eluent A/30% eluent B. The HPLC trace of crude PEP2667 is shown in FIG. 4.

Figure 5:
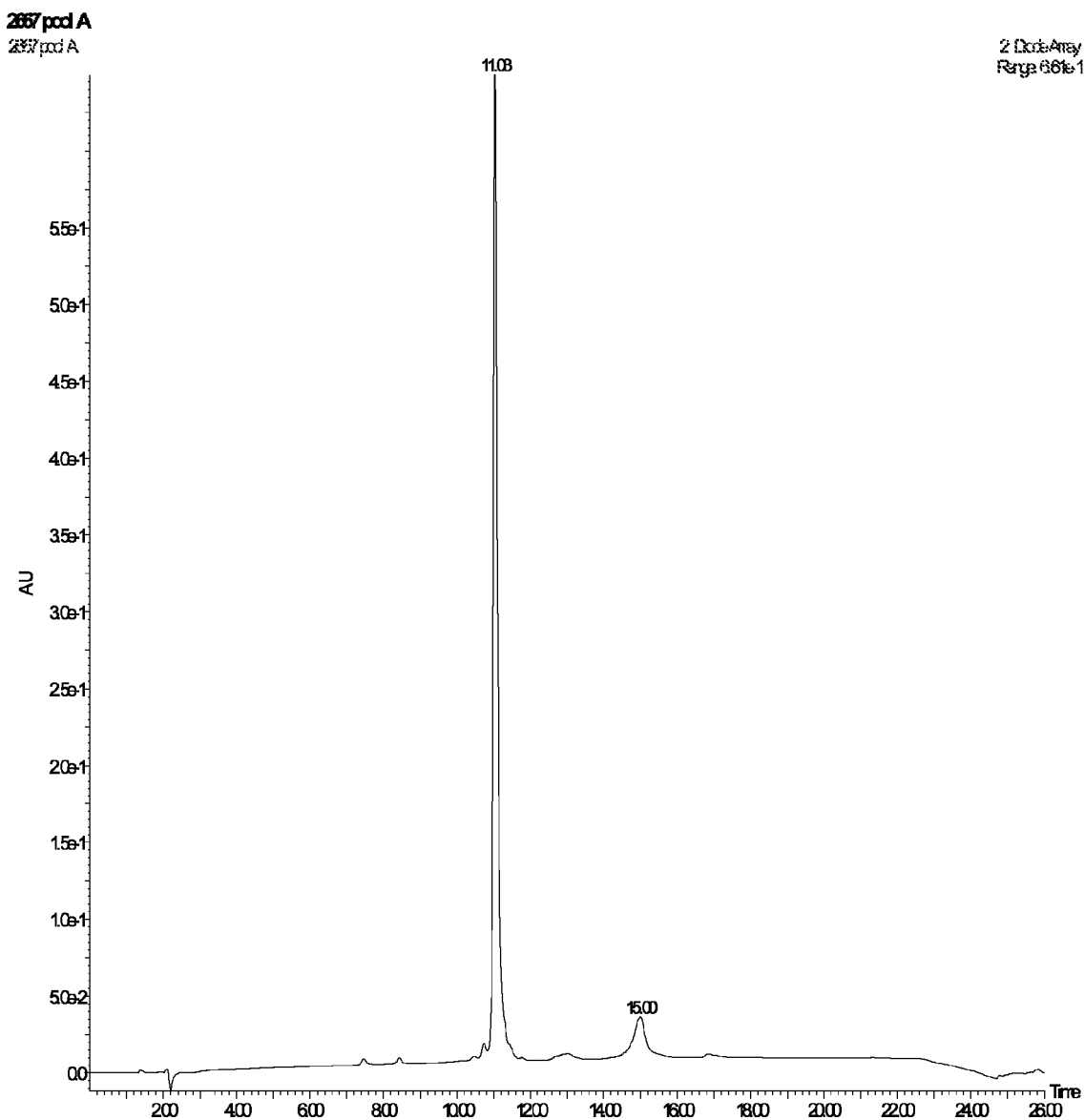
FIG. 5 shows the HPLC trace of purified PEP2667.

The crude peptide was purified by reverse-phase HPLC with semi-preparative Waters RCM Delta-Pak™ C$_{-4}$ cartridges (40×200 mm, 15 μm), using as eluents (A) 0.1% TFA in water and (B) 0.1% TFA in acetonitrile, and the following linear gradient: 35% (B)-50% (B) in 20'-80% (B) in 3'-80% (B) for 3', flow 80 ml/min. In a typical run 100 mg of crude PEP2667 were dissolved in 10 mL of 70% eluent A/30% eluent B and loaded onto the HPLC column. The HPLC profile of purified PEP2667 is shown in FIG. 5 (yield 20 mg, 20%) in which the minor peak eluting at higher t$_R$ (15 min) does not represent an impurity, since it appears also in the blank run.

The purified peptide was characterized by HPLC/MS on a Waters-Micromass LCZ platform as described above (theoretical M.W. 4594 Da, found 4592.6 Da).

REFERENCE EXAMPLE 3

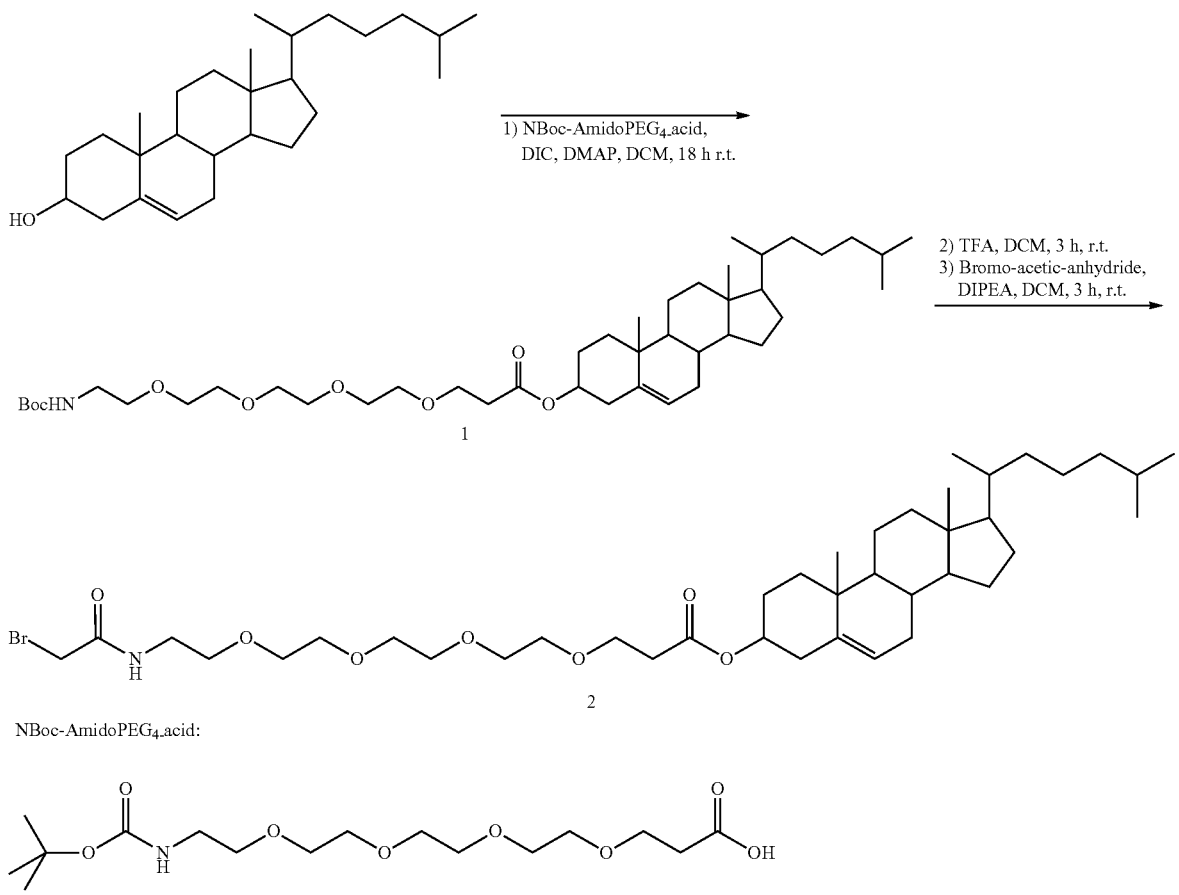

Cholest-5-en-3-yl 2,2-dimethyl-4-oxo-3,8,11,14,17-pentaoxa-5-azaicosan-20-oate (1):

N-t-boc-amido-dPEG$_4$™ acid (1 g, 2.7 mmol, Product N° 10220, Quanta BioDesign, Ltd.) was added to a solution of cholesterol (0.99 g, 2.7 mmol) in 40 mL of CH$_2$Cl$_2$, followed by N,N'-diisopropylcarbodiimide (0.43 mL, 3.2 mmol) and 4-dimethylamino-pyridine (16 mg, 5%). The mixture was stirred at room temperature overnight and the solvent was evaporated under vacuo. The crude was dissolved in EtOAc, washed with HCl 1N, saturated NH$_4$Cl and brine, dried over Na$_2$SO$_4$, filtered and concentrated. The crude was purified by flash column chromatography (BIOTAGE) on silica gel with a gradient 25-50% EtOAc in petroleum ether to afford 1.48 g of desired compound as incolor oil (Yield 75%).

Cholest-5-en-3-yl 1-bromo-2-oxo-6,9,12,15-tetraoxa-3-azaoctadecan-18-oate (2)

Trifluoroacetic acid (2 mL, 26 mmol) was added to a solution of 1 (1.48 g, 2 mmol) in 10 ml of CH$_2$Cl$_2$ and the mixture was stirred at room temperature for 3 h. All the volatiles were removed under vacuo and the crude was lyophilized to obtain an incolor oil that was dissolved in 60 mL of CH₂Cl₂. Bromoacetic anhydride (0.62 g, 2.4 mmol) was added followed by N,N-diisopropylethylamine (0.65 mL, 3.7 mmol) and the mixture was stirred at room temperature for 3 h. The solvent was removed under vacuo and the crude purified by flash column chromatography on silica gel (BIOTAGE) with a gradient 50-90% of EtOAc in petroleum ether to obtain 1.1 g of desired compound as a colourless oil with a yield of 74% in two steps.

EXAMPLE 1

Synthesis of (C34-Cholesterol): cholesteroylation Ac-WMEWDREINNYTSLIHSLIEESQN-QQEKNEQELLGSGC(Cholesteryl)-NH₂ (SEQ ID NO:1)

C34-Cholesterol was prepared by chemoselective thioether conjugation between the products of Reference Examples 1 and 2 in solution. 12 mg of purified Reference Example 2 (2.61 µmol) were dissolved in 600 µL of DMSO and 1.59 mg of Reference Example 1 (3.13 µmol, 1.2 eq), dissolved in 100 µL of THF, were added. Then 7 µL (1% by volume) of DIEA (N,N-diisopropyl-ethylamine) were added to the mixture which was left stirring at room temperature. The reaction was monitored by liquid chromatography-mass spectrometry using a Waters-Micromass LCZ Platform with a Phenomenex, Jupiter C₄ column (150×4.6 mm, 5 µm) using as eluents (A) 0.1% TFA in water and (B) 0.1% TFA in acetonitrile, and the following linear gradient: 30% (B)-70% (B) in 20'-80% (B) in 3'-80% (B) for 3', flow 1 ml/min.

Figure 6:
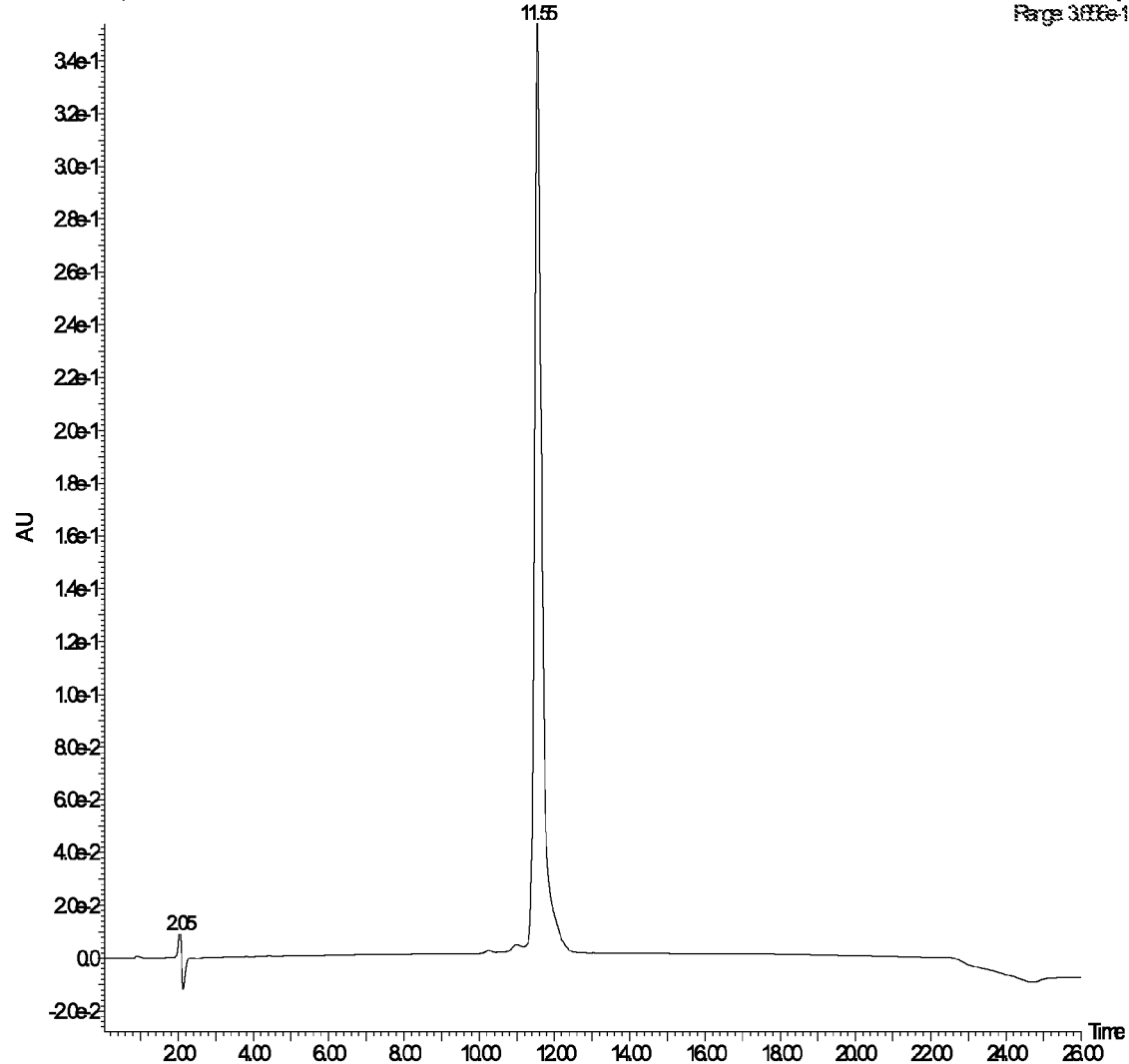
FIG. 6 shows the HPLC trace of purified C34-cholesterol.

After 1h incubation the reaction was complete and the cholesterol-peptide product was purified by reverse-phase HPLC with semi-preparative Waters RCM DELTA-PAK™ C₄ cartridges (25×200 mm, 15 µm), using as eluents (A) 0.1% TFA in water and (B) 0.1% TFA in acetonitrile, and an isocratic step at 50%(B) for 5' followed by the linear gradient: 35%(B)-50%(B) in 20'-80%(B) in 3'-80%(B) for 3', flow 30 ml/min. The purified peptide was characterized by HPLC/MS on a Waters-Micromass LCZ platform as described above but using the following linear gradient: 50%(B)-70%(B) in 20'-80%(B) in 3'-80%(B) for 3', flow 1 ml/min (theoretical M.W. 5020.0 Da, found 5020.7 Da). The HPLC profile of purified C34-Cholesterol is shown in FIG. 6 (yield 5.7 mg, 48%):

EXAMPLE 2

Synthesis of C34-(Oxa₄)-Cholesterol

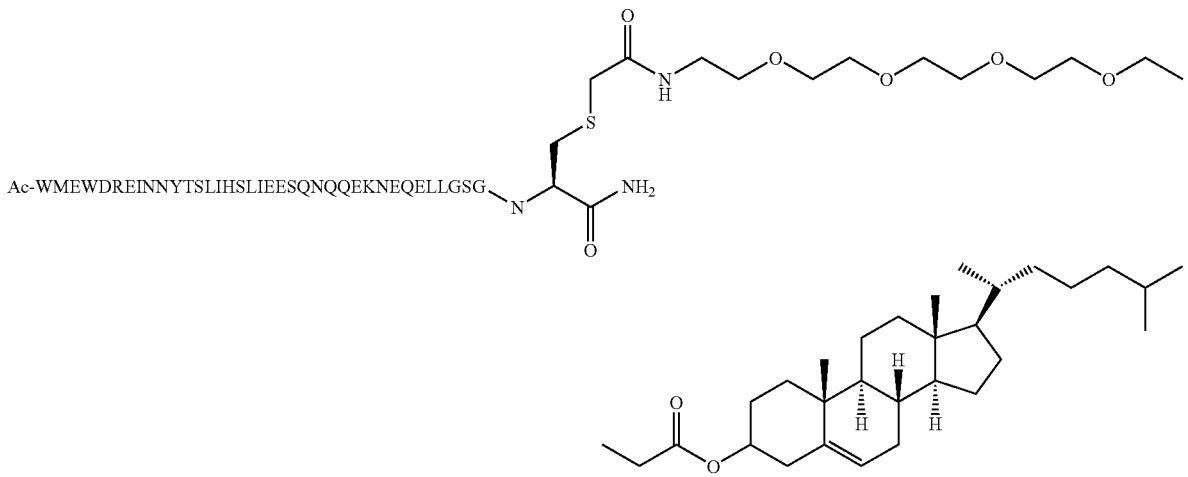

Acetyl-WMEWDREINNYTSLIHSLIEESQN-QQEKNEQELLGSGC(Oxa₄-Cholesterol)-NH₂ (SEQ ID NO.1)

Peptide C34-(Oxa₄) Cholesterol was prepared by chemoselective thioether conjugation between the product of Reference Example 2 and the product of Reference Example 3 in solution. 10 mg of purified Reference Example 2 (2.26 µmmol) were dissolved in 600 µL of DMSO and 1.88 mg of Reference Example 3 (2.49 µmol 1.1 eq), dissolved in 188 µL of THF, were added. Then 8 µL of DIEA (N,N-diisopropylethylamine) were added to the mixture which was left stirring at room temperature. The reaction was monitored by liquid chromatography-mass spectrometry using a Waters-Micromass LCZ Platform with a Phenomenex, Jupiter C₄ column (150×4.6 mm, 5 µm) using as eluents (A) 0.1% TFA in water and (B) 0.1% TFA in acetonitrile, and the following linear gradient: 35% (B)-80% (B) in 20'-80% (B) in 3'-80% (B) for 3', flow 1 ml/min.

After 3h incubation the reaction was complete and the cholesterol-peptide product was purified by reverse-phase HPLC with semi-preparative Waters RCM DELTA-PAK™ C₄ cartridges (25×200 mm, 15 µm), using as eluents (A) 0.1% TFA in water and (B) 0.1% TFA in acetonitrile, and an isocratic step at 50%(B) for 5' followed by the linear gradient: 50%(B)-70%(B) in 20'-80%(B) in 3'-80%(B) for 3', flow 30 ml/min. The purified peptide was characterized by HPLC/MS on a Waters-Micromass LCZ platform as described above but using the following linear gradient: 50%(B)-70%(B) in 20'-80%(B) in 3'-80%(B) for 3', flow 1 ml/min (theoretical M.W. 5268.0 Da, found 5267.7 Da). Yield: 4.7 mg.

The invention claimed is:
1. An inhibitor of viral fusion which is:

SEQ ID NO. 1
Ac-WMEWDREINNYTSLIHSLIEESQNQQEKNEQELLGSG—N

; or

SEQ ID NO. 1
Ac-WMEWDREINNYTSLIHSLIEESQNQQEKNEQELLGSG—NH

;

or a pharmaceutically acceptable salt thereof.

2. A pharmaceutical composition comprising an inhibitor of claim 1, or a pharmaceutically acceptable salt thereof, and a pharmaceutically acceptable excipient.

3. A pharmaceutical composition according to claim 2 which is a pessary, vaginal ring, cream or gel.

* * * * *

UNITED STATES PATENT AND TRADEMARK OFFICE
CERTIFICATE OF CORRECTION

PATENT NO. : 8,629,101 B2
APPLICATION NO. : 12/738998
DATED : January 14, 2014
INVENTOR(S) : Pessi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 575 days.

Signed and Sealed this
Twenty-second Day of September, 2015

Michelle K. Lee
*Director of the United States Patent and Trademark Office*